United States Patent [19]

Rodahl et al.

[11] Patent Number: 6,006,589
[45] Date of Patent: Dec. 28, 1999

[54] PIEZOELECTRIC CRYSTAL MICROBALANCE DEVICE

[75] Inventors: Michael Rodahl; Fredrik Höök; Anatol Krozer, all of Göteborg; Bengt Kasemo, Mellerud, all of Sweden

[73] Assignee: O-Sense AB, Gothenburg, Sweden

[21] Appl. No.: 08/913,885

[22] PCT Filed: Apr. 3, 1996

[86] PCT No.: PCT/SE96/00576

§ 371 Date: Sep. 25, 1997

§ 102(e) Date: Sep. 25, 1997

[87] PCT Pub. No.: WO96/35103

PCT Pub. Date: Nov. 7, 1996

[30] Foreign Application Priority Data

May 4, 1995 [SE] Sweden .................................. 9501653

[51] Int. Cl.[6] .................................................. G01N 11/10
[52] U.S. Cl. ........................ 73/54.41; 73/32 A; 310/316
[58] Field of Search ...................... 73/579, 23.36, 73/24.01, 24.06, 31.05, 31.06, 61.49, 61.61, 61.62, 32 A, 54.41; 310/316, 317, 321, 329

[56] References Cited

U.S. PATENT DOCUMENTS

| | | | |
|---|---|---|---|
| 3,653,253 | 4/1972 | Olin | 73/28 |
| 4,788,466 | 11/1988 | Paul et al. | 73/32 A |
| 5,485,744 | 1/1996 | Kutagawa et al. | 73/61.49 |
| 5,604,335 | 2/1997 | Isahaya | 73/24.01 |
| 5,734,098 | 3/1998 | Kraus et al. | 73/61.62 |
| 5,827,947 | 10/1998 | Miller et al. | 73/24.06 |

FOREIGN PATENT DOCUMENTS

| | | |
|---|---|---|
| 2 149 109 | 6/1985 | United Kingdom . |
| 2 236 855 | 4/1991 | United Kingdom . |

Primary Examiner—Michael Brock
Assistant Examiner—Helen C. Kwok
Attorney, Agent, or Firm—Burns, Doane, Swecker & Mahtis, L.L.P.

[57] ABSTRACT

A device and a process for measuring resonant frequency and dissipation factor of a piezoelectric resonator are presented. After exciting the resonator to oscillation, the driving power to the oscillator is turned off after the decay of the oscillation of the resonator is recorded and used to give a measure of at least one of the resonators properties, such as dissipation factor, changes in the dissipation factor, resonant frequency and changes in the resonant frequency.

20 Claims, 5 Drawing Sheets

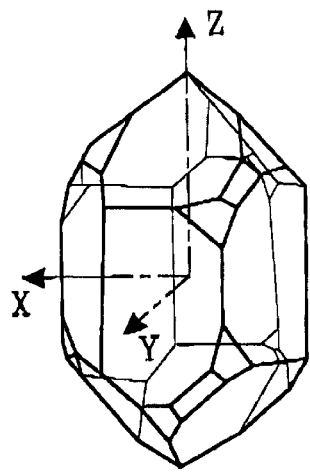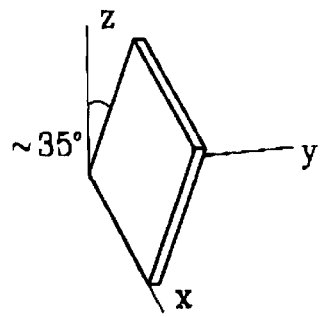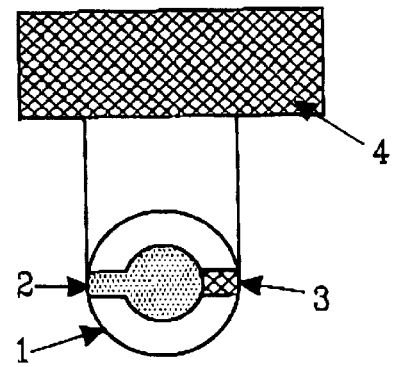
FIG.1a  FIG.1b  FIG.1c
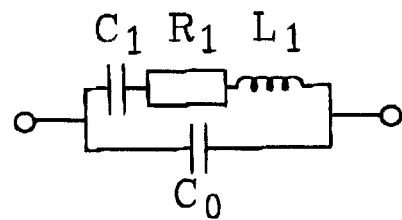
FIG.2
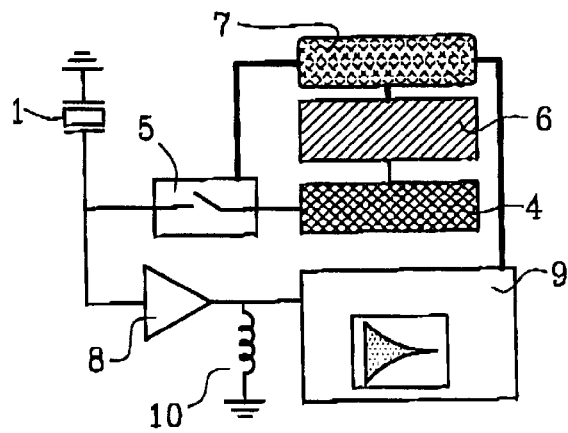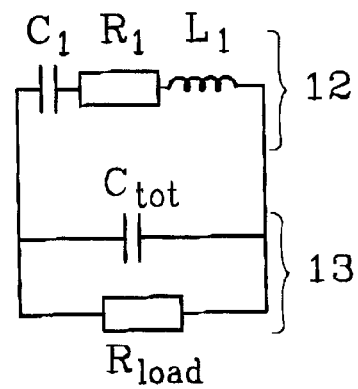
FIG.3a  FIG.3b

PIEZOELECTRIC CRYSTAL MICROBALANCE DEVICE

DESCRIPTION OF THE INVENTION

Background of the Invention

The invention relates to a device for measurement of the resonant frequency and the dissipation factor of a piezoelectric resonator, preferentially of the quartz crystal microbalance (QCM) type (where quartz crystal constitutes the sensing piezoelectric material). This type of device (the QCM) uses a single crystal quartz disk coated with electrodes of appropriate shape. The electrodes are connected to electrical circuitry that induces oscillations in the quartz.

The quartz crystal microbalance, QCM, is known to be an extremely sensitive weighing device. It is often used to weigh small amounts of matter which has been either removed from the quartz electrode(s) or may have been deposited onto one (or both) of the electrodes, usually as a thin film. (For details see, e.g., *Applications of piezoelectric quartz crystal microbalances*, C. Lu and A. W. Czanderna, Editors. 1984, Elsevier: Amsterdam; J. F. Alder and J. J. McCallum, *The Analyst*, 1983. vol. 108 p. 1291; G. G. Guilbaut *Ion-Selective Electrode Review*, 1980. vol. 2: p. 3; and D. A. Buttry in *Electroanalytical Chemistry*, A. J. Bard, Editor. 1991, Marcel Dekker, Inc.: New York. p. 1.)

Below we exemplify the function of the device using as an example a so-called AT-cut quartz sensor, FIG. 1b (for an illustration of the crystallographic axes of quartz see FIG. 1a). This is not to be contrued as a limitation on the invention. Other sensor materials, and/or quartz sensors cut to other crystallographic direction(s)—e.g. BT-cut, SC-cut, etc.—will function in a similar manner. The AT-cut sensor vibrates in a shear mode with an amplitude of about 1 nm at a fundamental resonant frequency, $f$, given by:

$$f = \text{constant} \cdot d^{-1} \quad (1)$$

where d is the thickness of the quartz plate. For example, if d is 0.17 mm, $f$ is approximately 10 MHz. The quartz sensor starts to oscillate if an AC electric field with a frequency centered close to the fundamental resonant frequency of the sensor is applied perpendicularly to its surfaces. Usually, electrodes on each side of the sensor plate are deposited by evaporation and are subsequently contacted to an external AC field generator (for example to a signal generator, or to an oscillator drive circuit, or the like). Under favorable condition this arrangement is capable of sensing mass changes smaller than 1 ng/cm$^{-2}$.

Ideally the mass changes, $\Delta m$, at the sensor electrode(s), induce a shift in the resonance frequency of the sensor, $\Delta f$, proportional to the mass changes:

$$\Delta f = -C \Delta m \quad (2)$$

where C, the proportionality constant, depends on the thickness of the quartz plate.

Equation (2) is valid provided that the mass is attached rigidly to the electrode and follows the oscillatory motion of the sensor without dissipative losses. Equation (2) may fail when the added mass is viscous or is not rigidly attached to the electrode(s) and can thus suffer elastic or plastic deformation(s) during oscillations. The relation between added mass and the shift of the resonant frequency then becomes more complex. The latter situation arises when for example a water droplet is deposited onto an electrode of the quartz sensor.

When the validity of Eq. (2) can be questioned, it becomes particularly important to obtain additional information about the properties of the added matter such as viscosity and/or the strength with which the added matter {film, particle(s) droplet(s)} is attached to the sensor electrode. The dissipation factor, D, of the QCM contains at least part of this information (the dissipation factor is defined as an inverse of the quality factor, Q,—a quantity commonly used in the oscillating devices). Thus, it would be of importance for the QCM technique if both $\Delta f$ and $\Delta D$ (the changes in the resonant frequency and the dissipation factor, respectively) could be measured simultaneously, especially in complex situations when Eq. (2) is no longer valid.

It is possible that additional information on the properties of a deposit and on its interaction with the sensor electrode can be obtained by exciting the quartz plate to oscillate in its overtone modes (3rd, 5th, etc.) and simultaneously measure $\Delta f$ and $\Delta D$ for each overtone. It is also possible that further information can be obtain by changing the crystallographic cut of the quartz wafer and measure $\Delta f$ and $\Delta D$ for a different excitation mode, e.g., the thickness extensional mode.

SUMMARY OF THE INVENTION

The purpose of this invention is to present a technical solution which would enable simultaneous measurements of $f$ and D, or $\Delta f$ and $\Delta D$. Measuring principle is based on an abrupt decoupling of the sensor driving circuitry from the resonator and monitoring the decay of the quartz sensor oscillation. When the driving circuitry is abruptly turned off from the sensor, the oscillation amplitude decays with time very much like a toll of a church bell which gradually weakens after being hit by a clapper. The speed with which the oscillation amplitude decays is inversely proportional to D, i.e. the time constant for decay, $\tau$, $\tau \, 1/D$. If a high impedance probe, or a low impedance probe, is used to measure said amplitude decay, the quartz sensor oscillates in its parallel mode, or in its series mode, respectively, during the decay. Thus, given that both the amplitude and the frequency of oscillation during a decay are measured, we obtain a set of four possible quantities that can be measured (i) the resonant frequency for parallel oscillation mode $f_p$, (ii) the resonant frequency for series oscillation mode, $f_s$, (iii) the decay constant for parallel oscillation mode $D_p$, and (iv) the decay constant for series oscillation mode, $D_s$. The invention enables one to perform these four measurements several times per second with a sensitivity and resolution that allows one to detect changes in $\Delta f_{p,s}$ ($\Delta f_s$ or $\Delta f_p$) and $\Delta D_{p,s}$ ($\Delta D_s$ or $\Delta D_p$) corresponding to less than a monolayer of added matter, and to perform these measurements either in vacuum, gaseous, or liquid environment. The invention allows these measurements to be performed at either the fundamental resonant frequency or one (or more) of the overtones. The device and the process disclosed herein may be used in a variety of applications such as, for example, measurement of phase transitions in thin films, the detection of adsorption of biomolecules, and measurements of the viscoelastic properties of thin films.

BRIEF DESCRIPTION OF THE DRAWINGS

FIGS. 1a–1c shows schematic drawings of the crystallographic axes of quartz, an AT-cut slab of quartz, and an AT-cut quartz crystal connected to a driving apparatus.

FIG. 2 shows an equivalent electric circuit describing electrical properties of the QCM in the vicinity of resonance.

FIGS. 3a–3b shows an example of an experimental setup for simultaneous frequency and dissipation factor measurements.

DETAILED DESCRIPTION OF THE INVENTION

Figure 4:
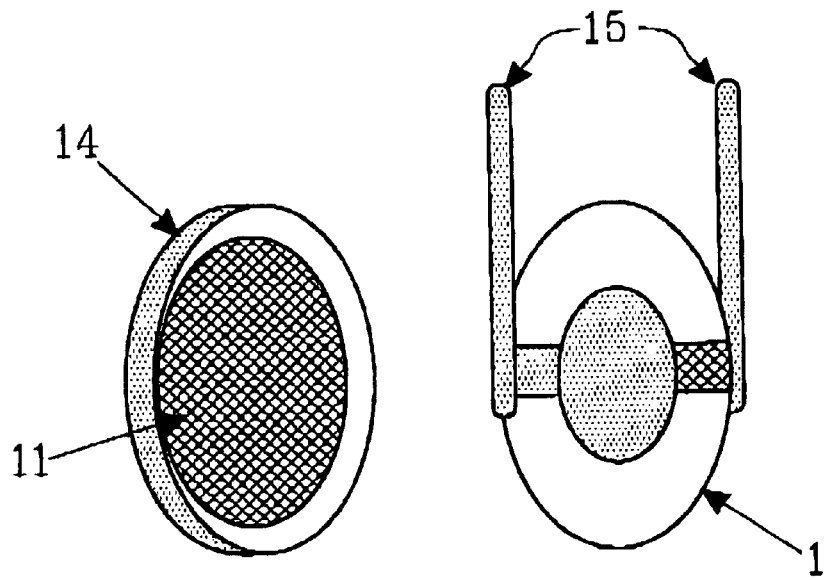
FIG. 4 shows an example of an electrode configuration.

Before describing the technical side of our invention a short theoretical background to the invention is appropriate. It is well known that an AT-cut quartz crystal oscillates in a so-called shear mode when driven by the varying electric field. This field is applied to the electrodes 2 and 3 deposited on each side of the sensor crystal 1 and connected to an electric driving circuitry 4 (FIG. 1c). The AT-cut belongs to a family of so-called Y-cuts characterized by the fact that all Y-cut quartz plates oscillate in a shear mode when driven by an external AC-field. As pointed out earlier, this well known device is capable of measuring extremely small amounts of matter deposited onto, or removed from, the sensor electrodes 2 and 3. Ideally, the measured resonant frequency shift $\Delta f$ is proportional to $\Delta m$ in accordance with Eq. (2).

As pointed out earlier, the proportionality between $\Delta f$ and $\Delta m$ expressed by Eq. (2) does not necessarily hold when the matter deposited onto the electrode(s) of the quartz sensor is viscous, if it is not rigidly attached to the electrode, or when it deforms elastically or plastically during an oscillation period. More information about properties of the deposited matter such as its viscosity, or stiffness, the strength of the attachment of the film, droplet, etc., to the electrode surface, etc., are then needed to, e.g., be able to accurately convert a measured $\Delta f$ into the corresponding change in mass. Part of this information can be obtained by measuring the dissipation factor.

The dissipation factor, D, is defined as:

$$D = \frac{1}{Q} = \frac{E_{dissipated}}{2\pi E_{stored}}, \quad (3)$$

where $E_{dissipated}$ is the energy dissipated during one oscillation cycle while $E_{stored}$ is the energy stored during one oscillation period. For a typical AT-cut quartz crystal with resonant frequency 10 MHz that oscillates in air or in vacuum D varies between $10^{-6}$–$10^{-4}$. However, D increases drastically if a sensor is immersed into a liquid, or a liquid droplet is deposited onto the electrode(s).

FIG. 2 shows the equivalent electric circuit for a QCM close to the resonant frequency—assuming that all the parasitic vibration modes of the sensor in the vicinity of the fundamental frequency are suppressed and can be neglected. The resonance conditions for oscillation occur either when the imaginary part of the total impedance is equal to zero (short circuited equivalent circuit of the quartz sensor) or when the imaginary part of the total impedance is infinite (open circuit). The sensor is said to oscillate in its series mode in the former case, and in its parallel mode in the latter case. With reference to the equivalent circuit in FIG. 2, D can be expressed as:

$$D = \frac{R_1}{\omega L_1}, \quad (4)$$

where $\omega = 2\pi f$ is the circular resonant frequency, while $R_1$ and $L_1$ are defined in FIG. 2. For a simple harmonic oscillator, as the one depicted in FIG. 2, $\omega$ is related to D via:

$$\omega = \omega_0 \sqrt{1 - D^2/2} \approx \{D \ll 1\} \approx \omega_0, \quad (5)$$

where $\omega_0$ is the resonance frequency when the dissipation is negligible. The maximal oscillation amplitude at resonance is given by $$A = \frac{B}{D\sqrt{1 - D^2/4}} \approx \{D \ll 1\} \approx \frac{B}{D}, \quad (6)$$

where B is the driving force divided by the force constant.

The total energy loss for the QCM device is given by the sum of individual losses in the system, i.e. the total dissipation factor $D_{tot}$ is given by $$D_{tot} = \sum_i D_i, \quad (7)$$

where $D_i$ is the dissipation factor of the subsystem i. Energy losses in a QCM setup include contributions from, e.g., internal friction in the quartz itself, losses due to mounting of the crystal, etc. In most applications, the contribution due to losses caused by the deposited film is by far the most dominant. If a deposited film slides on the electrode, energy is lost due to friction. The coefficient of friction can in this case be determined by measuring the dissipation factor of the system. If the deposited material is viscous, energy is lost due to the excitation of a damped shear wave in the deposit, i.e., due to an internal friction in the deposit. If D can be measured with sufficient resolution and sensitivity, it is possible to obtain additional information about the deposited matter regarding, e.g., its viscosity or friction coefficient between the electrode and the film.

If a matter is adsorbed from liquid onto one (or both) of the electrodes of the QCM, the increase of the dissipation due the adsorbed mass is superimposed on the contribution to D from the liquid itself. The viscoelastic coupling between the electrode and the liquid can be modified by an adsorbed monolayer of, e.g., protein, and thereby affect D.

In studies of overlayers using the QCM technique, several researchers have observed that changes, or rearrangements, in the film structure can cause a change in D (see, for example, A. Widom, and J. Krim, *Physical Review B-Condensed Matter*, 1986, vol. 34, p. 1403 and V. M. Mecea, *Sensors and Actuators A*, 1993, vol. 40, p. 1). In all these studies, D was estimated by measuring the peak-to-peak value of the output voltage from an oscillator. Given that the peak-to-peak value of the output voltage is proportional to the oscillation amplitude, one obtains, according to Eq. (5), that it also is inversely proportional to D. This method is relatively simple, but suffers from several drawbacks: (i) It requires that the external driving force is constant, i.e., the feedback in the oscillator circuitry must be linear, since otherwise the proportionality between the peak-to-peak value of the output and the oscillation amplitude cannot be assured. (ii) It cannot be used together with automatic gain control (AGC). This is a severe limitation since it has been observed that the crystal sensor immersed in a liquid solution is oscillating only within a narrow driving-force interval. To meet this requirement, AGC is often used, whereby the driving force matches the load on the crystal. (iii) It does not give an absolute value of D. Therefore a calibration for each sensor/driving circuit pair is necessary. These disadvantages are avoided using the method presented here.

Instead of using the output voltage from the oscillator to measure the oscillation amplitude, the present procedure is based on the method used by Spencer and Smith in their study of the amount of defects in quartz (W. J. Spencer, and W. L. Smith, J. Appl. Phys. 37, p. 2557 (1966)). It is based on the fact that when the driving power (the force exciting the oscillations) is switched off, the amplitude of oscillation decays exponentially. Spencer and Smith measured the decay of the amplitude of oscillation using an oscilloscope by taking a photograph of the oscilloscope screen. From this photograph, they visually estimated the decay time constant which is, as mentioned above, inversely proportional to D.

We have considerably developed and modified the original setup of Spencer and Smith to allow for full automation of the simultaneous measurement of the amplitude of oscillation, the resonant frequency ($f_s$ or $f_p$), and the dissipation factor ($D_s$ or $D_p$). In the present invention, both the amplitude and the resonant frequency are recorded after the driving force has been switched off. When the force driving a piezoelectric, harmonic oscillator is switched off at t=0, the voltage over the crystal, A, decays as an exponentially damped sinusoidal:

$$A(t) = A_0 e^{-t/\tau} \sin(\omega t + \phi) + \text{constant}, \, t \geq 0, \qquad (8)$$

where $A_0$ is the amplitude of oscillation, $\tau$ is the time constant of the decaying signal, $\phi$ is its phase, and the "constant" in Eq. (8) is the DC-offset value. The decay time constant is related to $D_{tot}$ as:

$$D_{tot} = \frac{2}{\omega \tau}. \qquad (9)$$

$A_0$, $\tau$ and $\omega$ are obtained by fitting Eq (8) to the recorded decay curve. The dissipation factor is then given by Eq. (9).

Furthermore, the crystal can itself can constitute a part of an oscillator circuit, which eliminates the need of an expensive high-precision signal generator used by Spencer and Smith. This can be an advantage since the crystal is at all times optimally driven at its resonant frequency also when the resonant frequency changes during prolonged experiment. For example, measurements of the frequency changes which occur when adsorption isotherms or phase transitions are followed can take several hours or even days. Of course, a signal generator can be used instead of an oscillator, if that for some reason is wanted—e.g., if the crystal is loaded heavily and can not be used in an oscillator circuit.

The following examples are provided to illustrate the present invention and are not to be construed as a limitation thereon.

EXAMPLE 1

FIG. 3a shows one example of how an experimental setup for the simultaneous $f$ and D measurements may be implemented. This setup was used in measurements described in the examples 2–9, below. A measurement of $f$ and D includes the following steps: (i) The computer 7 triggers the relay 5 to close whereupon the crystal 1 starts to oscillate by the action of the oscillator 4. (ii) The crystal 1 is allowed to oscillate until the oscillation is stable, typically for about 20 ms. (iii) Next the computer 7 simultaneously triggers the relay 5 to open and the oscilloscope 9 to start a measurement. (iv) The curve recorded on the oscilloscope 9 is transferred to the computer 7 which is programmed to perform a fit to Eq. (8), using the Levenberg-Marquardt method. If the frequency counter 6 is used to measure the resonant frequency during the excitation by the oscillator about one second of measuring time is added before step (iii) above.

We have tested this setup using AT-cut, 10 MHz QCM-crystals obtained from Quartz Pro Instruments AB, and with 6 and 5 MHz QCM-crystals obtained from Maxtec Inc. One electrode of the crystal sensor was connected to ground whereas the other was connected to the driving oscillator 4 via a relay 5 (Clare, MSS-2). Stable oscillation for all crystals tested was achieved 20 ms after closing of the relay.

The resonant frequency, with the oscillator connected, was measured in the "traditional" way using a frequency counter 6 (Philips PM 6680). The counter 6 was controlled by a computer 7 equipped with a GPIB card. A Burr-Brown 3553 buffer amplifier connected between the crystal 1 and the relay 5 was used as a high impedance probe 8. In this setup, the crystal oscillates in the series mode when the crystal is driven by the oscillator and in its parallel mode during the decay after the relay has opened. The computer 7 controlled the relay via a DA-converter and fetched the decay curve from the oscilloscope 9 (LeCroy 9450A) using the GPIB card. The curve was fitted to Eq. (8) using the Levenbera-Marquardt method. From the fit the amplitude, the decay time constant, $\tau$, and the resonant frequency ($f_p$) are obtained.

The main differences between our technical solution and that of Spencer and Smith are the following: (i) Our solution allows simultaneous measurements of the oscillation amplitude of the crystal sensor, of its resonant frequencies ($f_s$ and $f_p$) and of the absolute dissipation factors, $D_s$ and/or $D_p$. (ii) Our solution is fully automated. (iii) The crystal can be a part of an oscillator circuit in the present solution eliminating the need of an expensive high-precision frequency generator. (iv) Using a digitizing oscilloscope, as in the presented setup, the recorded decay curve can be numerically fitted to Eq (8). Thereby a much higher precision in the determination of D, compared to Spencer and Smith, can be achieved.

When the relay 5 disconnects the crystal 1 from the driving circuit 4, there may remain a voltage over the crystal (DC-offset voltage) equal to the voltage delivered by the driving circuit 4 at that particular instance. The decaying signal voltage (amplituide) is thus superimposed on a DC-offset which can have any value between $-A_0$ and $A_0$. Therefore, the voltage setting on the oscilloscope must allow for a voltage range of $3A_0$. To avoid this large voltage range, a high-pass filter 10 was used to eliminate the DC-offset. Using a high-pass filter 10 the voltage range detected by the oscilloscope 9 is at most $2A_0$. Thereby, the resolution of the measured decay curve is increased.

The decay curve was sampled with a sampling frequency, $f_m$, of about 100 kh. Due to aliasing, the recorded signal has an apparent frequency, $f_r$, lower than the true frequency, $f$, of the signal:

$$f_r = \frac{\text{frac}\left(\frac{f}{f_m}\right)}{\frac{1}{f} + \frac{1}{f_m}} \quad (10)$$

where "frac" means the decimal part Eq. (10) is only valid if $$\text{frac}\left(\frac{f}{f_m}\right) < 0.5.$$

The recorded signal can therefore be fitted to either $f_r$ or $f$. (It is of course possible to mix the signal from the crystal 1 with a reference signal and record the difference frequency and thus avoid aliasing.)

It is important that the relay and the probe do not significantly contribute to the energy dissipation of the oscillating crystal, since this would increase $D_{tot}$ and introduce a systematic error in the measured $D_{tot}$. When the relay is open, the load, $Z_{load}$ 13, on the crystal can be represented by a resistor, $R_{load}$ and a capacitance, $C_{tot}$, in parallel with the crystal 1 as shown in FIG. 3b. In this example, the resistance of the relay and the probe are $10^8$ Ω and $10^{11}$ Ω, respectively. $C_{tot}$ is the sum of all capacitances in parallel with the crystal, including the capacitance of the probe (~25 pF), $C_0$, and stray capacitances in the circuit The losses in contacts and cables were estimated to be negligible. The total loss in the measurement is given by the real part of $Z_{load}$ 13 ($Z_{load}$ is the total load impedance seen by the crystal), which can be expressed as:

$$\text{Re}(Z_{load}) = X_{load} = \frac{R_{load}}{1 + (\omega C_{tot} R_{load})^2}. \quad (11)$$

This loss should be compared with $R_1$ in Eq (4). Hence, the additional "parasitic" loss $D_e$, as:

$$D_e = \frac{X_{load}}{R_1} D_0, \quad (12)$$

where $D_0$ is the "true" dissipation factor, that is the one which would have been measured if the probe and the relay were ideal, i.e., of infinite impedance. Typically, $R_1$=10 Ω and $C_0$=5 pF for a 10 MHz AT-cut crystal oscillating in air. If we disregard stray capacitances, $X_{load}$ can be estimated to 3mΩ. The parasitic dissipation is in that case about 0.3%. We want to point out that if only the changes in the dissipation factor are of interest, then the "parasitic" dissipation factor is cancelled out In a liquid, $R_1$ increases considerably (to about 300 Ω) and the "parasitic" dissipation factor will therefore be smaller, relatively speaking.

In the setup used in the present example, the crystal 1 was driven by the oscillator circuit 4 for about 20 ms before each measurement, i.e., before the relay 5 was opened. Data transfer from the oscilloscope 9 to the computer 7, took about 300 ms. Summing up, this results in a samling rate of about 3 Hz.

Upon oscillation, the QCM usually dissipates about 2–150 μW. This can cause a slight temperature increase of the quartz sensor. The magnitude of the temperature increase depends, among other things, on the heat capacity of the crystal holder and of the surrounding medium. Although this temperature increase is usually small, it can be important in applications which require a crystal wafer in equilibrium with its surroundings. This is for example the case in studies of phase transitions and other critical phenomena. In the presented setup (FIG. 3) the crystal 1 is not connected to the oscillating circuit 4 in-between measurements (i.e., for most of the time), and the heating effect is minimized compared to continuous driving of the crystal 1.

For measurements in vacuum and gaseous environments, the crystal was held in place by the electrical connections 15 to the oscillator 1 (see FIG. 4). This setup exposed both of the electrodes 2 and 3 to the surroundings. To avoid short-circuiting of the electrodes 2 and 3 when the crystal was used in a conducting liquid, one of the electrodes was covered with a Macor® (Corning) lid 14 glued onto the quartz wafer 11 using silicon (see FIG. 4). The electrode exposed to the solution was connected to electrical ground. This arrangement is of advantage if simultaneous electro-chemistry measurements are performed, since the grounded electrode can be used as one of the electrodes in an electrochemical cell circuit.

EXAMPLE 2

Figure 5:
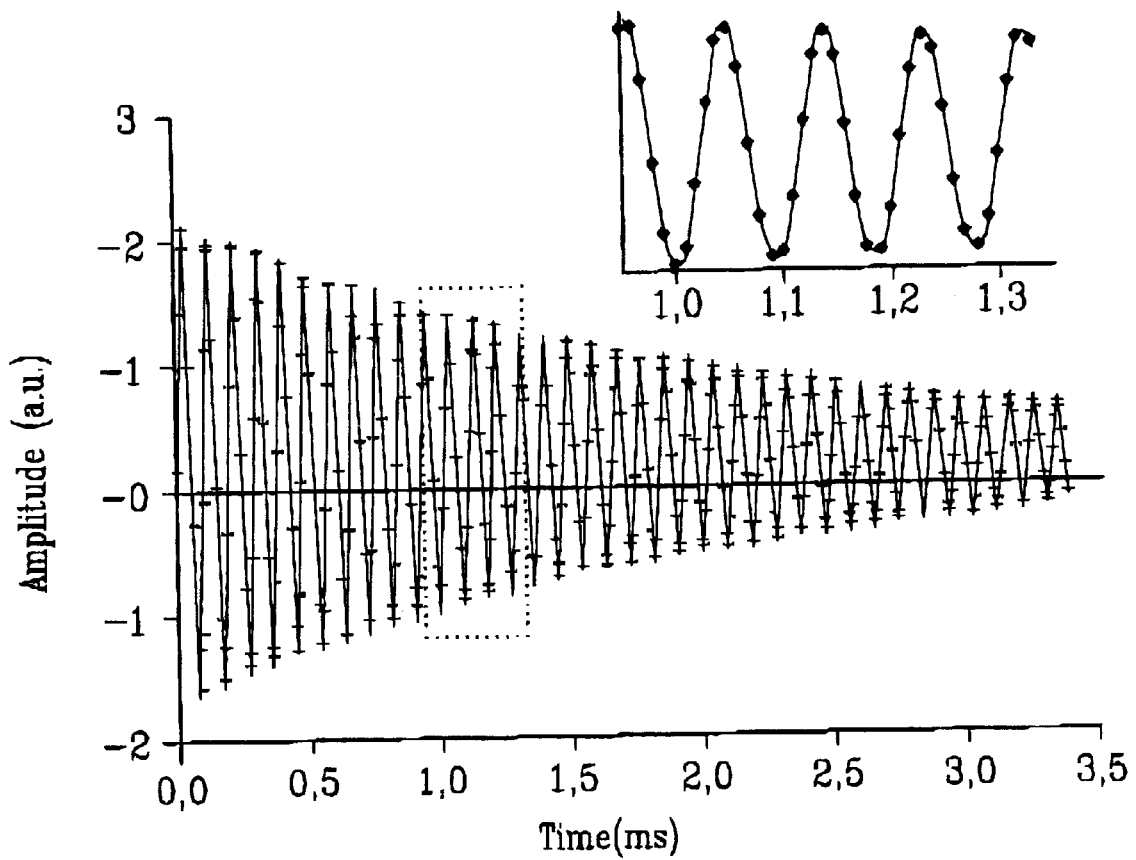
FIG. 5 presents a trace of a typical oscillation decay (after the driving power has been turned off) for an 10 MHz, AT-cut quartz crystal oscillating in air.

FIG. 5 shows a typical decay curve for 10 MHz, AT-cut quartz crystal sensor operating in air. The inset shows enlargement of the area within a dashed box in the main figure. The crosses are the measured points and the solid line is the curve fitted according to Eq. (8). The apparent resonant frequency is lower than 10 MHz due to so-called aliasing.

EXAMPLE 3

Figure 6:
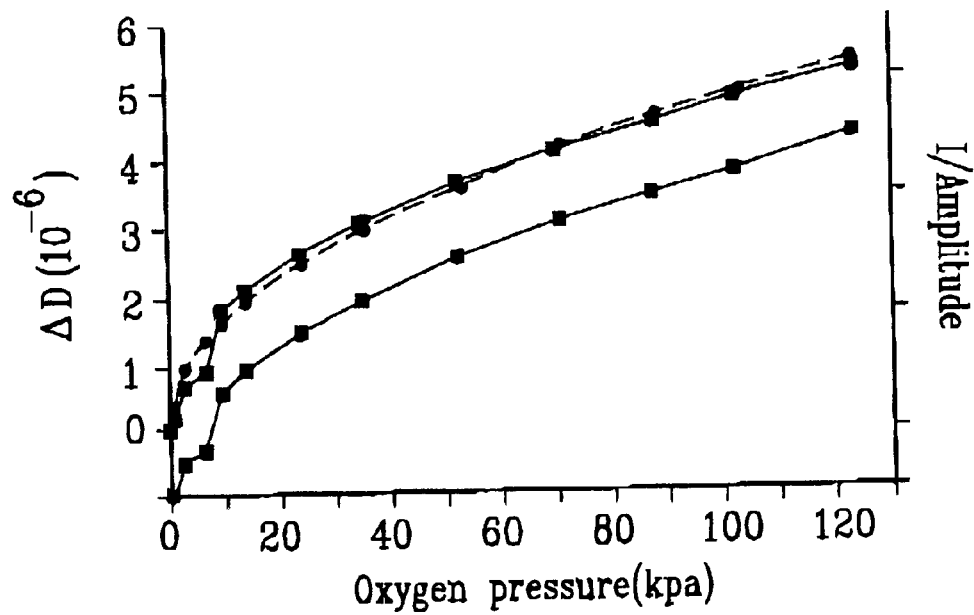
FIGS. 6–11 shows changes in the frequency and the dissipation factor, measured using the setup shown in FIG. 3, of the sensor subject to different experimental conditions.

FIG. 6 shows the change in the dissipation factor for a 10 MHz, AT-cut QCM as a function of oxygen pressure in the measuring chamber. The filled circles and the dotted line are the theoretical values while the diamonds represent the measured values. The measured values of the inverse of the amplitude of oscillation are shown as filled squares.

The theoretical expression for the dissipation due to the gas pressure, $D_g$, has been given by Stockbridge (in *Vacuum Microbalance Techniques* Plenum Press, 1966, vol. 5, p. 147) as $$D_g = \frac{4}{\rho_q t_q} \sqrt{\frac{\rho_g \eta_g}{2\omega}} \sqrt{\frac{\omega \tau_r}{1 + (\omega \tau_r)^2} \left( \sqrt{1 + \frac{1}{(\omega \tau_r)^2}} + 1 \right)}$$

where $\rho_g$ and $\eta_g$ are the gas density and viscosity, respectively. $t_q$ is the thickness of the quartz plate, and $\tau_r$ is the mean time for a gas molecule to loose $e^{-1}$ of the kinetic energy it aquired after the collision with the sensor surface. $\tau_r$ is generally expressed as $N\tau_c$, where N is an integer and $\tau_c$ is the mean time between collisions in the gas phase.

EXAMPLE 4

Figure 7:
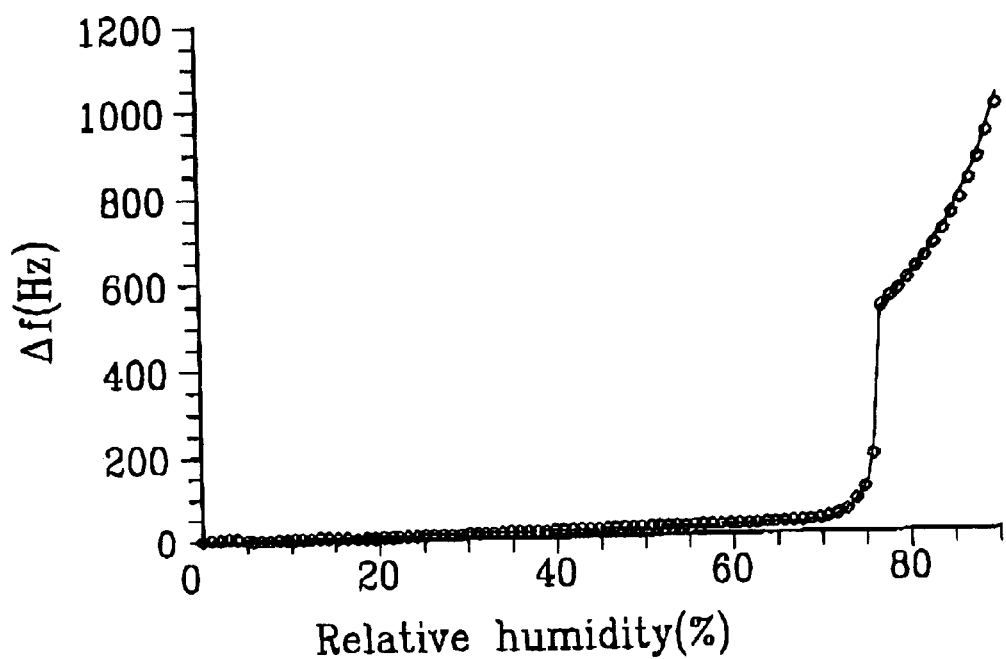

FIG. 7 shows a comparison between the change in resonant frequency as calculated from the curve fit to the decay curve (diamonds) and as measured with a frequency counter (solid line). Approximately 3 nm thick NaCl film was evaporated onto one of the QCM electrodes. The relative humidity was slowly varied between 0% and 90%. As expected, the change in resonant frequency measured using the decay curves agrees very well with the one measured using the frequency counter.

EXAMPLE 5

Figure 8:
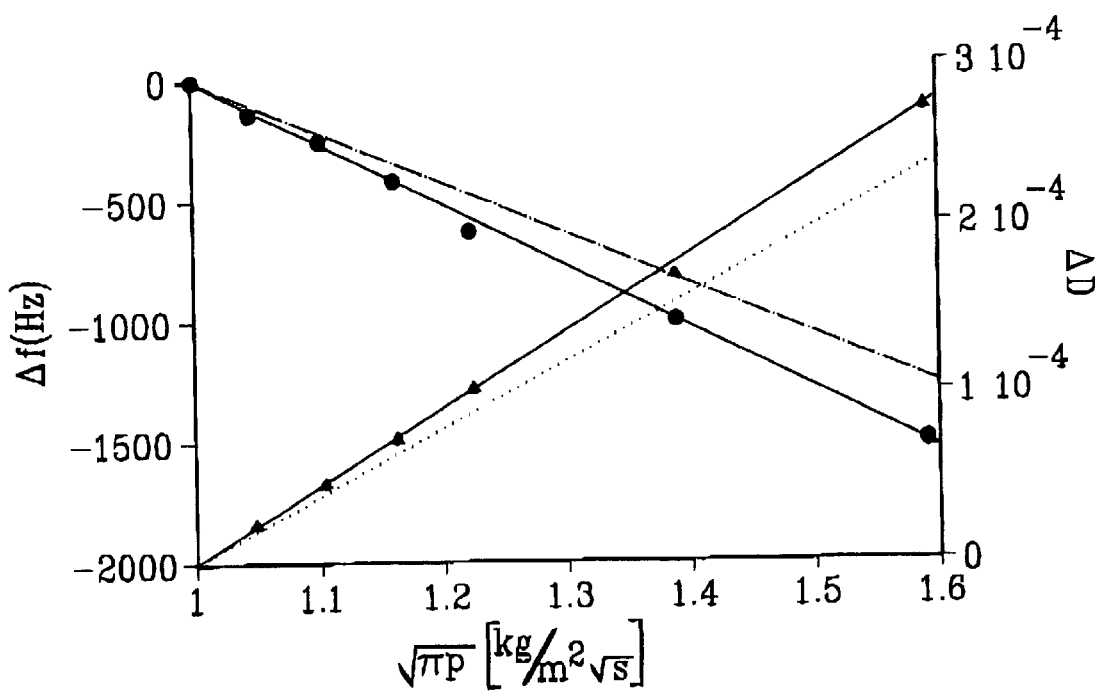

FIG. 8 shows the changes in $f$ and D as a function of $\sqrt{\eta_l \rho_l}$ for a AT-cut 10 MHz QCM with one side exposed to air and the other side immersed into water-glucose mixtures. ΔD and Δf have been set to 0 for pure water. $\eta_l$ and $\rho_l$ are the fluid viscosity and density, respectively. The solid lines are the best linear fits to the measured values and the dashed lines are the theoretical values.

EXAMPLE 6

Figure 9:
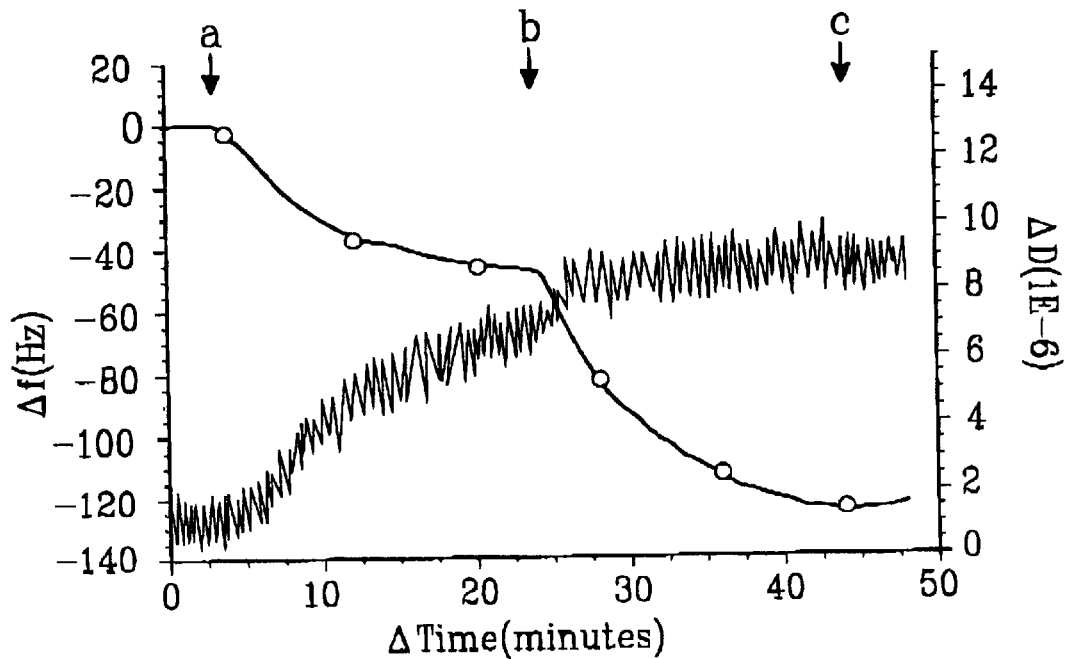

FIG. 9 shows the changes in $f$ and D for a 5 MHz AT-cut crystal with thiol treated gold electrodes, due to the adsorption of fibrinogen and subsequently antifibrinogen from a buffer solution flowing over one side of the crystal. The experiment starts with pure buffer flowing over the crystal at time=0. At the time marked by a, the pure buffer was replaced by a buffer containing approximately 25 mg/l fibrinogen. At the time marked by b, the flow was changed to a buffer containing approximately 25 mg/l antifibrinogen. At the time marked by c, the flow was switched to a pure buffer again. Adsorption took place only on one side of the crystal (the electrode exposed to the liquid flow). The sampling rate was approximately 30 data points per minute.

EXAMPLE 7

Figure 10:
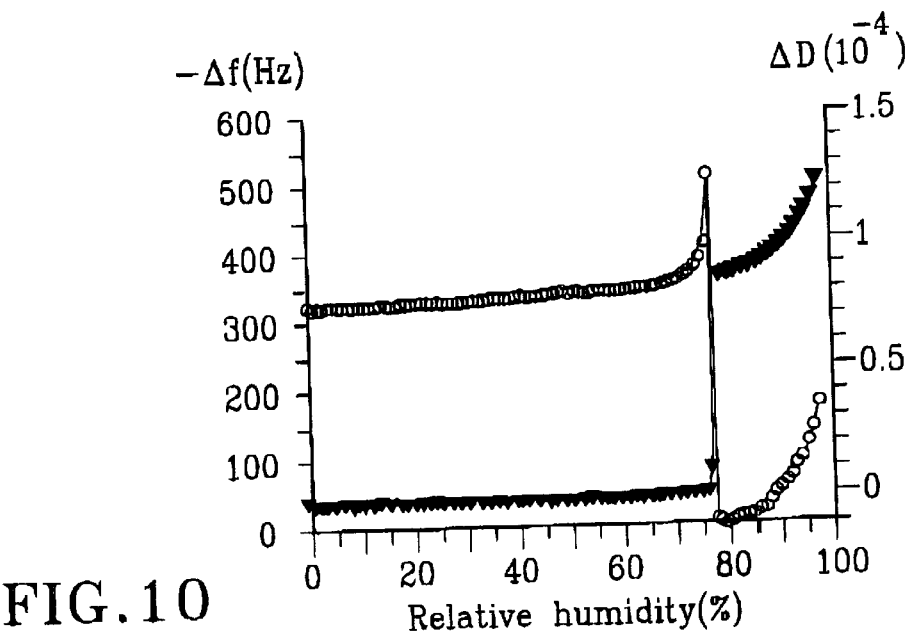

FIG. 10 shows the change in $f$ (open circles) and D (filled triangles) of a 10 MHz, AT-cut QCM coated with 19 nm thick layer of NaCl as a function of relative humidity. Note that a measurement of Δf alone could be interpreted (according to Eq. (2)) as a decrease in mass when humidity is increased above 76% relative humidity. The measurement of D, however, indicates that the overlayer is becoming viscous and therefore Eq. (2) cannot be used. Below 75% relative. humidity the film is a solid but above 77% relative humidity it has undergone a phase transition to liquid (salt water).

EXAMPLE 8

Figure 11:
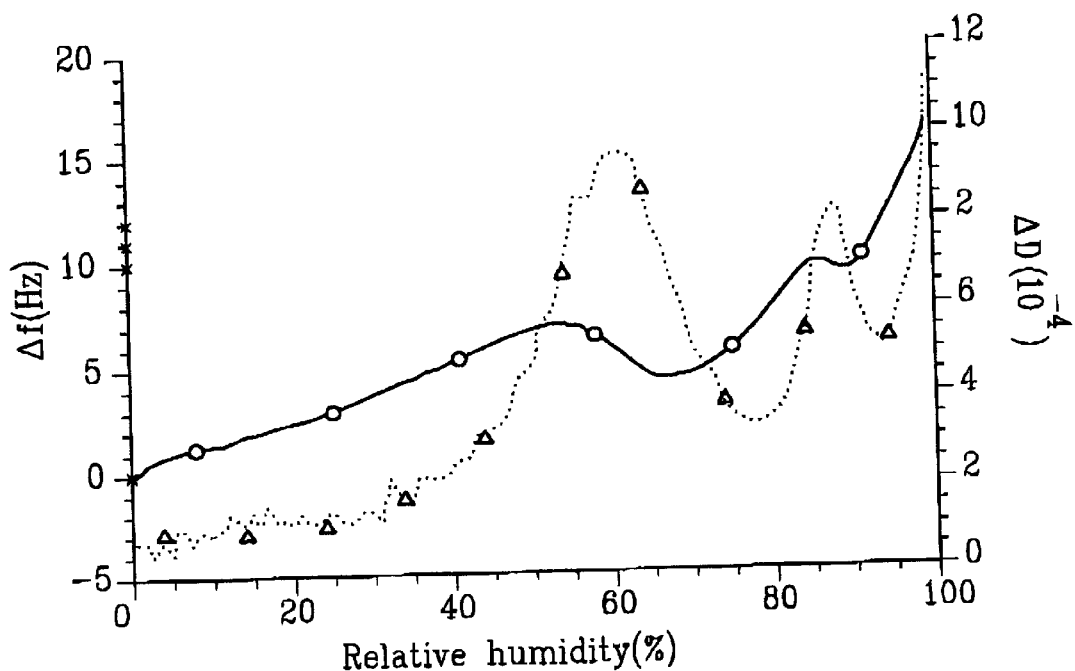

FIG. 11 shows the measured change in $f$ (solid line with circles) and D (dotted line with triangles) as a function of relative humidity for a 10 MHz AT-cut QCM with gold electrodes. The relatively large change in D can tentatively be explained by the sliding of the adsorbed water (from the humid air) on the substrate (the gold electrode). (The viscous losses in molecularly thin films are extremely small and can be neglected.) If the adsorbed water film did not slide on the substrate, one monolayer of rigidly adsorbed water would correspond to approximately 11 Hz. Due to the imperfect coupling between the motion of the crystal and the motion of the film, the resonant frequency shift becomes somewhat smaller, approximately 8 Hz (the peak at 55% relative humidity).

What is claimed is:

1. A device for determining properties of a piezoelectric resonator, wherein a piezoelectric crystal is connected to a driving apparatus in order to make said crystal oscillate, said device comprising:

means for exciting the crystal to oscillation using a driving power supplied by said driving apparatus, means for turning off the driving power to said crystal, means for recording the decay of an oscillation amplitude and a resonant frequency of said crystal as a function of time, and means for using said recorded decay to measure at least one of a dissipation factor of said crystal and changes in said dissipation factor, and at least one of a resonant frequency of said crystal and changes in said resonant frequency.

2. The device of claim 1, wherein said means for using said recorded decay measures automatically.

3. The device of claim 1, wherein said crystal is set up to operate in at least one of vacuum, gas, and liquid phases.

4. The device of claim 1, wherein the measurement is performed at a fundamental resonant frequency of said crystal and at overtones of said crystal.

5. The device of claim 1, wherein the measurement is performed on different types of crystals and different crystallographic cuts.

6. The device of claim 1, wherein said device further comprises means for determining biomolecule adsorption kinetics and uptake of said crystal, and said adsorption's effect of said crystal's dissipation factor.

7. The device of claim 1, said crystal having at least one electrode, wherein said at least one electrode constitutes an electrode in an electrochemical cell.

8. The device of claim 1, wherein the measurement is used to study phase transitions.

9. The device of claim 1, wherein said means for turning off the driving power involves abruptly turning off the driving power to said crystal.

10. The device of claim 1, wherein said means for using said recorded decay measures simultaneously.

11. A method for determining properties of a piezoelectric resonator wherein a piezoelectric crystal is connected to a driving apparatus in order to make said crystal oscillate, said method comprising:

exciting the crystal to oscillation using a driving power supplied by said driving apparatus, turning off the driving power to said crystal, recording decay of an oscillation amplitude and a resonant frequency of said crystal as a function of time, and using said recorded decay to measure at least one of a dissipation factor of said crystal and changes in said dissipation factor, and at least one of a resonant frequency of said crystal, and changes in said resonant frequency.

12. The method of claim 11, wherein the measurement is automatic.

13. The method of claim 11, wherein said crystal is set up to operate in at least one of vacuum, gas, and liquid phases.

14. The method of claim 11, wherein the measurement is performed at a fundamental resonant frequency of said crystal and overtones of said crystal.

15. The method of claim 11, wherein the measurement is performed on different types of crystals and different crystallographic cuts.

16. The method of claim 11, wherein said method further comprises the step of determining biomolecule adsorption kinetics and uptake of said crystal, and said adsorption's effect of said crystal's dissipation factor.

17. The method of claim 11, wherein said crystal has at least one electrode, and wherein said at least one electrode constitutes an electrode in an electrochemical cell.

18. The method of claim 11, wherein the measurement is used to study phase transitions.

19. The method of claim 11, wherein said step of turning off the driving power involves abruptly turning off the driving power of said crystal.

20. The method of claim 11, wherein the measurement is simultaneous.

* * * * *